US012589012B2

(12) United States Patent
Ding et al.

(10) Patent No.: US 12,589,012 B2
(45) Date of Patent: Mar. 31, 2026

(54) SYSTEM AND METHOD FOR BRAIDING A PATIENT-CUSTOMIZED STENT

(71) Applicant: Acandis GmbH, Pforzheim (DE)

(72) Inventors: Andreas Ding, Karlsruhe (DE); Andrés Braschkat, Bretten (DE); Manuel Kälber, Niefern Öschelbronn (DE)

(73) Assignee: Acandis GmbH, Pforzheim (DE)

( * ) Notice: Subject to any disclaimer, the term of this patent is extended or adjusted under 35 U.S.C. 154(b) by 770 days.

(21) Appl. No.: 17/794,198

(22) PCT Filed: Jan. 12, 2021

(86) PCT No.: PCT/EP2021/050452
    § 371 (c)(1),
    (2) Date: Jul. 20, 2022

(87) PCT Pub. No.: WO2021/148277
    PCT Pub. Date: Jul. 29, 2021

(65) Prior Publication Data
    US 2023/0355412 A1     Nov. 9, 2023

(30) Foreign Application Priority Data

Jan. 21, 2020    (DE) ..................... 10 2020 101 250.0

(51) Int. Cl.
    *A61F 2/90*        (2013.01)
(52) U.S. Cl.
    CPC .......... *A61F 2/90* (2013.01); *A61F 2240/004* (2013.01); *A61F 2250/0064* (2013.01)
(58) Field of Classification Search
    CPC ... D04C 3/40; D04C 3/42; D04C 3/44; D04C 3/46; D04C 3/48
    See application file for complete search history.

(56) References Cited

U.S. PATENT DOCUMENTS

| | | | |
|---|---|---|---|
| 4,509,877 A * | 4/1985 | Sobin ..................... | F16C 1/262 |
| | | | 403/41 |
| 4,846,908 A * | 7/1989 | Aldrich ................... | B29C 35/02 |
| | | | 156/149 |

(Continued)

FOREIGN PATENT DOCUMENTS

| | | |
|---|---|---|
| DE | 102013103176 A1 | 10/2014 |
| DE | 102015107291 A1 | 9/2015 |
| WO | WO-2004/093966 A1 | 11/2004 |

OTHER PUBLICATIONS

German Office Action, patent application No. 10 2020 101 250.0 mailed Oct. 29, 2020, 8 pages.

(Continued)

*Primary Examiner* — Bao-Thieu L Nguyen
(74) *Attorney, Agent, or Firm* — Cesari and McKenna, LLP

(57) ABSTRACT

The disclosure relates to a system for braiding a patient-specific adapted stent. The system includes at least one set with multiple braiding sleeves and a base carrier for receiving at least two braiding sleeves of the set, wherein the braiding sleeves each have an inner contour adapted to the outer contour of the base carrier, so that multiple braiding sleeves can be arranged in any order on the base carrier, in particular slid in any order onto the base carrier, to form a braiding mandrel, and wherein at least two braiding sleeves of the set have different outer contours from each another. Furthermore, the invention relates to a method for braiding a patient-specific adapted stent.

19 Claims, 4 Drawing Sheets

(56) References Cited

U.S. PATENT DOCUMENTS

| | | | | |
|---|---|---|---|---|
| 5,645,559 A * | 7/1997 | Hachtman | D04C 3/48 | 606/198 |
| 6,047,756 A * | 4/2000 | Uchida | B29D 22/00 | 156/149 |
| 6,149,682 A * | 11/2000 | Frid | D04C 3/48 | 623/1.35 |
| 10,519,578 B2 * | 12/2019 | Zhang | D04C 1/02 | |
| 11,613,833 B1 * | 3/2023 | Head | B32B 1/08 | 428/34.1 |
| 2001/0015510 A1 * | 8/2001 | Nakamura | D04C 3/48 | 264/159 |
| 2003/0135265 A1 * | 7/2003 | Stinson | D04C 1/06 | 623/1.22 |
| 2004/0254633 A1 | 12/2004 | Rapaport | | |
| 2005/0137680 A1 * | 6/2005 | Ortiz | A61F 2/90 | 623/1.53 |
| 2014/0137722 A1 * | 5/2014 | Huang | D04C 1/06 | 156/149 |
| 2015/0209134 A1 * | 7/2015 | Cully | A61B 17/12122 | 623/1.13 |
| 2018/0289466 A1 | 10/2018 | Soletti et al. | | |
| 2021/0137715 A1 * | 5/2021 | Ringwala | A61F 2/90 | |
| 2021/0346181 A1 * | 11/2021 | Tieu | A61F 2/86 | |
| 2023/0011914 A1 * | 1/2023 | Lu | D04C 1/06 | |
| 2024/0113373 A1 * | 4/2024 | Gutierrez | H01M 50/236 | |

OTHER PUBLICATIONS

PCT Notification of Transmittal of the International Search Report and the Written Opinion of the International Searching Authority, or the Declaration, International Searching Authority, International Application No. PCT/EP2021/050452, mailed Apr. 19, 2021, 12 pages.

* cited by examiner

SYSTEM AND METHOD FOR BRAIDING A PATIENT-CUSTOMIZED STENT

CROSS REFERENCE TO RELATED APPLICATIONS

The present application is a National Stage of International Application No PCT/EP2021/050452, filed Jan. 12, 2021, which application claims priority to commonly owned German Patent Application No. 102020101250.0, filed on Jan. 21, 2020, which applications are incorporated herein by reference in their entirety.

TECHNICAL FIELD

The invention relates to a system for braiding a patient-specific adapted stent. Furthermore, the invention relates to a method for braiding such a stent.

BACKGROUND

From DE 10 2013 103 176 A1, originating from the applicant, a method for producing a patient-specific adapted stent is known, in which a corresponding braiding tool is produced on the basis of image data of a target vessel in a patient. Thereby, the image data is used to first create a virtual tool model. The tool model can then be modified. The tool model is then used to produce a braiding tool specifically adapted for the patient. Braiding of the stent from wires is performed on this braiding tool so that a stent is formed that is individually adapted for a predetermined target vessel in a patient.

The known method has the particular advantage that the stent produced in this way is excellently adapted to the contour of the target vessel and thus exhibits a particularly good therapeutic effect. However, in order to be able to use such a production method, it is necessary to have the appropriate equipment for this purpose. For the production of the patient-specific adapted stent according to known methods, it requires correspondingly high-quality imaging devices, image processing devices and devices for the production of a braiding tool. If imaging devices and corresponding image processing devices are not available on site in the hospital, a relevant logistic effort is necessary to be able to produce such a patient-specific adapted stent. The very precise but relatively complex production of the adapted stent is associated with a high time and cost expenditure.

In this respect, there is a need for a system that has similar advantages but is available quickly and at low cost.

SUMMARY

The task of the present invention is to provide such a system. In particular, the invention is intended to provide a system for braiding a patient-specific adapted stent that is available at low cost and quickly. Furthermore, it is a task of the invention to disclose a method for braiding a patient-specific adapted stent using such a system.

According to the invention, this task is solved with respect to the system by the subject-matter of patent claim 1 and with respect to the method by the subject-matter of patent claim 8.

The invention is based on the idea of providing a system for braiding a patient-specific adapted stent, the system comprising at least one set with multiple braiding sleeves and a base carrier for receiving at least two braiding sleeves of the set. The braiding sleeves each have an inner contour adapted to the outer contour of the base carrier, so that multiple braiding sleeves can be arranged in any order on the base carrier, in particular slid in any order onto the base carrier, to form a braiding mandrel. At least two braiding sleeves of the set have different outer contours from each another.

The invention uses a modular principle so that a braiding tool adapted to the blood vessel contour in the patient can be created from different existing braiding sleeves accordingly for the patient. For this purpose, the different braiding sleeves, which differ from each other in their outer contour, can be combined with each other as desired so that a braiding mandrel is formed whose outer contour corresponds as closely as possible to the inner contour of the blood vessel to be treated. It is true that it is not possible to achieve such an exact match with the inner contour of a blood vessel as is known from the prior art mentioned at the beginning. However, the system according to the invention is readily available and correspondingly cost-effective.

Corresponding sets of different braiding sleeves can be kept in stock by the stent manufacturer. Based on the image data of a patient, for example angiographic X-ray images, different braiding sleeves of the set can then be combined with each other to reproduce the vessel section to be treated as similarly as possible. In this way, the production of the stent can be accelerated by braiding filaments on such a braiding mandrel, thus reducing the time and cost required to produce a patient-specific adapted stent.

In the context of the present description, the term "filament" refers to an elongated, wire-like component that is sufficiently flexible to be braided. In particular, the filament may have a round cross-section. Other cross-sectional shapes (oval, polygonal, D-shaped, etc.) are possible. In this respect, the term "filament" serves as a generic term for wires or threads formed from a metal or a plastic, in particular a polymer. A wire or thread comprising a combination of metal and plastic is also referred to as a filament.

In a preferred embodiment, it can be provided that the at least two braiding sleeves of the set have different lengths from one another. The braiding sleeves can therefore differ not only in their outer contour but also in their length. It is not excluded that the set as a whole also comprises multiple braiding sleeves whose outer contour is essentially identical, but which differ in length. Furthermore, the set may also have several identical braiding sleeves. In any case, the aim is to provide a sufficient number of different braiding sleeves in the set so that the stent manufacturer can select the best possible combination of braiding sleeves for the production of a stent whose outer contour comes as close as possible to the inner contour of the vessel to be treated, according to the specifications of the treating physician, by means of a large number of possible combinations. At least two, preferably at least three, in particular at least four or more than four, braiding sleeves differ in their outer contour.

In a further preferred variant of the system according to the invention, it can be provided that at least one braiding sleeve of the set has an outer contour and/or length which is produced on the basis of image data of a blood vessel of an individual patient. The at least one braiding sleeve, which is produced on the basis of image data of a blood vessel of an individual patient, can be produced, for example, using a method described in DE 10 2013 103 176 A1 mentioned at the beginning. In this case, the braiding sleeve corresponds to the braiding tool mentioned in DE 10 2013 103 176 A1. The contents of DE 10 2013 103 176 A1 are accordingly incorporated here in their entirety. By producing a braiding sleeve based on image data of a blood vessel of an individual patient, the therapeutic effect of the later braided stent can be further improved. It is true that the production of a braiding sleeve, the outer contour of which is produced on the basis of the inner geometry of the blood vessel to be treated, increases the time required and thus the cost of production. However, this may be acceptable in individual cases, for example if an improvement in the success of the treatment is prioritized.

In order to be able to form the braiding mandrel as quickly and easily as possible from the at least two or more braiding sleeves, the base carrier preferably has at least one cylindrical carrier section, the braiding sleeves each having a through opening, so that the braiding sleeves can be slid onto the carrier section with a loose fit. The loose fit makes it easier to slide the braiding sleeves onto the base carrier, whereby any order of the braiding sleeves can be selected. At the same time, the loose fit is preferably configured or provided with such small tolerances that the braiding sleeves are essentially hardly movable in radial direction. This prevents the braiding sleeves from displacing radially with respect to the longitudinal axis of the base carrier during braiding of the stent.

The base carrier may further have, at a first longitudinal end of the carrier section, a first stop for the braiding sleeves. At a second longitudinal end of the carrier section, the base carrier may have an attachment section for receiving a removable, second stop. It is particularly preferred if a distance between the first stop and the second stop is variable such that the braiding sleeves slid onto the carrier section can be fixed longitudinal-axially between the first stop and the second stop.

In particular, by means of the attachment section, it is possible to fix the braiding sleeves on the base carrier in the axial direction so that longitudinal displacement of the braiding sleeves is prevented. The attachment section has a certain length so that the removable, second stop can be attached to the base carrier at different distances from the first stop. Depending on the combination of braiding sleeves selected, the overall length of the braiding mandrel formed by the braiding sleeves may differ. The attachment section makes it possible to place the second stop to the extent that a longitudinal axial fixation is achieved regardless of the respective selected combination and resulting length of the braiding sleeve combination.

The attachment section may have an external thread. The second stop can be formed by a threaded nut. The combination of a threaded nut as a stop and an external thread as a attachment section makes it particularly easy to fix the braiding sleeves longitudinally and axially to the carrier section of the base carrier. In particular, it is also possible to set different distances between the first stop and the second stop, with the length of the external thread essentially predetermining the possible distances.

A secondary aspect of the invention relates to a method for braiding a patient-specific adapted stent using a previously described system. The method according to the invention comprises the following steps:

selecting multiple braiding sleeves from the set, wherein at least two braiding sleeves have different outer contours from each other;

arranging the selected braiding sleeves on the base carrier to form a braiding mandrel, wherein the braiding sleeves directly abut each other; and braiding the stent from one or more filaments on the braiding mandrel.

Preferably, the step of selecting multiple braiding sleeves comprises the detection of the inner contour of a blood vessel to be treated with the stent and the targeted selection of braiding sleeves which in combination form an outer contour adapted to the inner contour of the blood vessel.

The outer contour adapted to the inner contour of the blood vessel may not completely match the inner contour of the blood vessel. However, by selecting multiple braiding sleeves from a set of preformed braiding sleeves, the stent manufacturer can determine an outer contour of a braiding mandrel that most closely matches the inner contour of the blood vessel based on the treating physician's planning. Since only from one set of multiple braiding sleeves has to be selected here, the formation of the braiding mandrel involves a small amount of time, so that an appropriately adapted stent can be produced quickly. Overall, this reduces the time to therapy.

The step of selecting multiple braiding sleeves may comprise selecting at least two and/or at most ten, in particular at least two and at most seven, in particular two or five, braiding sleeves. In this respect, the base carrier of the system is preferably adapted to receive at least three and/or at most ten, in particular at least three and at most seven, in particular three or five braiding sleeves. In particular, the carrier section can receive the aforementioned number of braiding sleeves.

When braiding a stent on a braiding mandrel whose outer contour varies, in particular whose cross-sectional diameter varies, the porosity of the stent usually also changes. In other words, the meshes of the stent become different in size due to the different cross-sectional diameters of the braiding mandrel. To avoid this, in a preferred variant of the method according to the invention, it is provided that a braiding angle is varied when braiding the stent so that a uniform porosity is established over the entire length of the stent. Thus, by varying the braiding angle in relation to the variation of the outer contour on the braiding mandrel, it can be avoided that the stent has different porosities. Alternatively, of course, it may be provided that the braiding angle is varied such that the porosity changes. In particular, a lower porosity can be set in a region of the braiding mandrel corresponding to a blood vessel section in which, for example, an aneurysm is located, than in other regions. In the other areas, on the other hand, the braiding angle can be reduced, for example, in order to achieve that the stent section braided in this way shortens slightly during expansion, i.e. the so-called "foreshortening" is reduced. In this way, stents can be produced that are adapted to specific therapeutic goals.

Furthermore, it is possible that in preferred embodiments of the method according to the invention, the braiding direction of a filament is reversed when braiding the stent, whereby loops are formed at one longitudinal end of the stent. Thus, in this embodiment, a stent is produced that has open filament ends at only one longitudinal end. On the opposite longitudinal end, however, loops are formed, reducing the risk of vascular injury in the blood vessel.

Furthermore, it is also possible that the stent as a whole is braided from only a single filament, whereby the braiding direction is reversed several times during the braiding of the stent, so that loops are formed at both longitudinal ends. The filament ends of the single filament can be arranged in the center of the stent and, in particular, connected to each other. In this way, a stent is formed that does not have any open filament ends.

It is particularly preferred if, in the method according to the invention, the stent is braided from filaments comprising an radiopaque core material and a sheath material of a shape memory alloy, in particular a nickel-titanium alloy. It may also be provided that only single filaments of the stent comprise such a radiopaque core material and a sheath material of a shape memory alloy. The remaining filaments may be formed from a shape memory alloy only.

Filaments that have a radiopaque core material and a sheath material made of a shape memory alloy are also referred to as DFT wires. The use of DFT wires has the advantage that the stent as a whole is visible over its entire length and also on the basis of its outer contour under X-ray control. This ensures that the stent is correctly placed in the blood vessel to be treated. Such exact positioning is particularly useful for patient-specific stents in order to achieve the best possible therapeutic success.

BRIEF DESCRIPTION OF THE DRAWINGS

The invention is explained in more detail below by means of an example of an embodiment with reference to the enclosed schematic figures. Therein show.

DESCRIPTION

Figure 1:
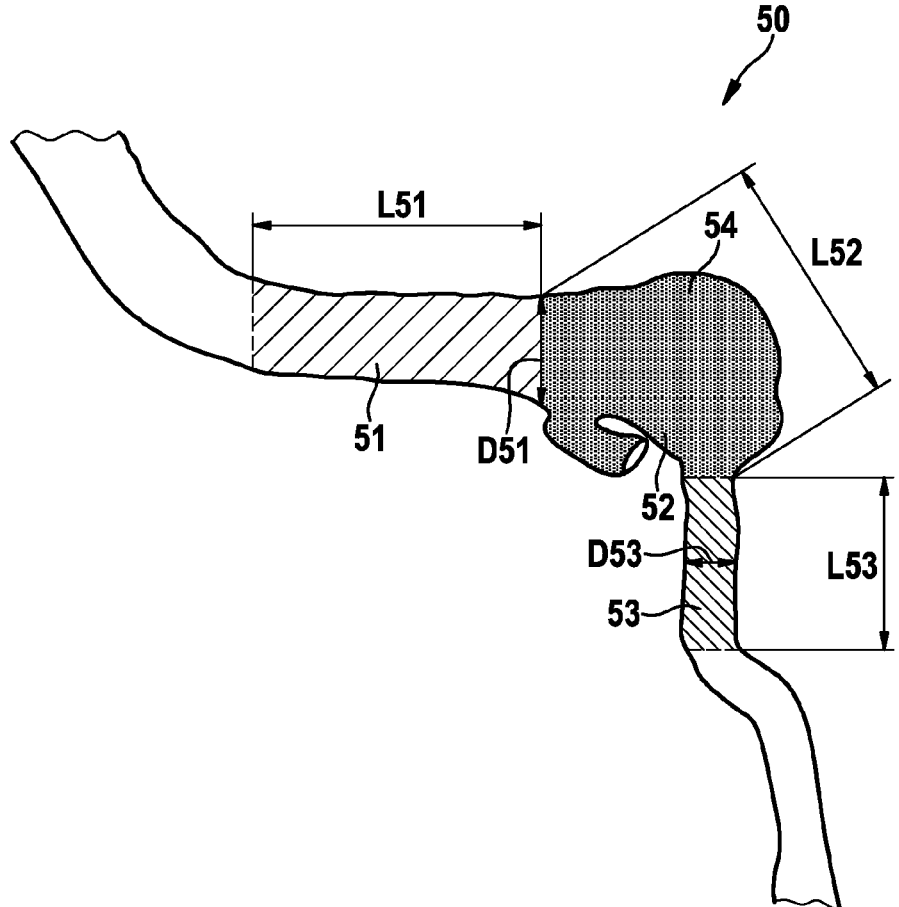
FIG. 1: a longitudinal section through a blood vessel to be treated from image data, which serve as a basis for producing a patient-specific adapted stent by means of the system according to the invention.

FIG. 1 shows a blood vessel 50 to be treated with a stent 10. The blood vessel 50 according to FIG. 1 is shown as an illustration by an image processing.

From X-ray images, the contour of the blood vessel 50 can be graphically reproduced, as shown in FIG. 1.

The blood vessel 50 has three segments 51, 52, 53. A proximal segment 51 comprises a length L51 and a diameter D51. A middle segment 52 comprises a length L52. A distal segment 53 comprises a length L53 and a diameter D53. The lengths L51, L52, L53 and diameters D51, 53 provide a total of five anatomical parameters based on which a stent 10 is to be produced to treat the blood vessel 50 with the aneurysm 54 located in the middle segment 52.

Figures 2, 3:
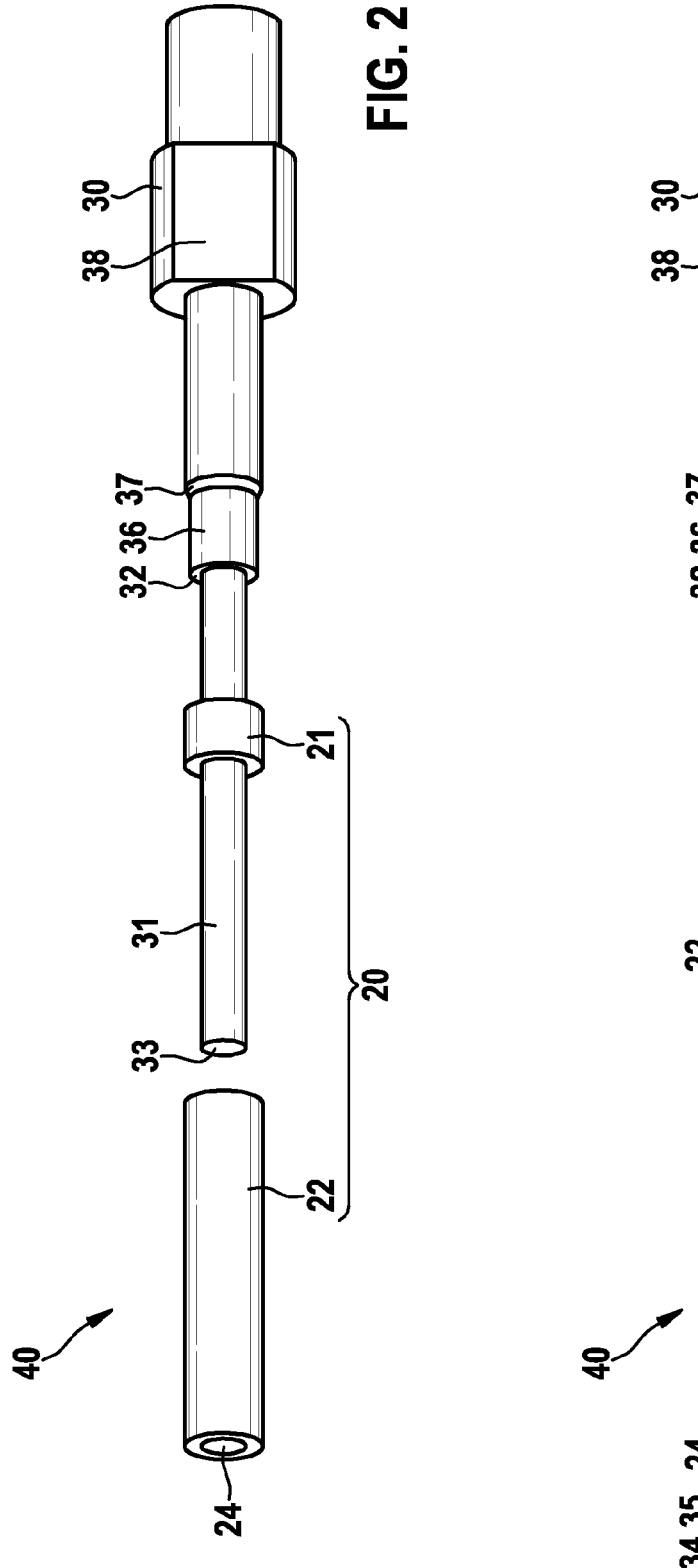
FIG. 2: a perspective view of a system according to the invention according to a preferred embodiment with a base carrier and two braiding sleeves.
FIG. 3: a perspective view of a system according to the invention according to a further preferred embodiment with three braiding sleeves.

To produce a corresponding stent 10, the invention provides a system comprising a set 20 of multiple braiding sleeves 21, 22, 23 and a base carrier 30, as shown for example in FIGS. 2 and 3.

FIG. 2 shows an embodiment example with a base carrier 30 and a set 20, which together form a braiding mandrel 40. For this purpose, the base carrier 30 comprises a carrier section 31 onto which the individual braiding sleeves 21, 22, 23 can be slid. The braiding sleeves 21, 22, 23 each comprise a through opening 24 therefor, which can be slid onto the cylindrical carrier section 31 with a loose fit. In the embodiment example according to FIG. 2, the set 20 comprises multiple braiding sleeves 21, 22, 23, of which two braiding sleeves 21, 22 have been selected to form the braiding mandrel 40 together with the base carrier 30. It can be seen that the two braiding sleeves 21, 22 differ in their outer contour and their length. Specifically, the first braiding sleeve 21 has a frustoconical outer contour. The second braiding sleeve 22 is cylindrical in shape and comprises a multiple of the length of the first braiding sleeve 21.

The base carrier 30 comprises on the one hand the carrier section 31 and on the other hand an attachment section 33 at a distal end of the base carrier 30. The attachment section 33 is shown in the schematic illustration according to FIG. 2 merely as a cylindrical extension of the carrier section. The same applies to FIG. 3. In practice, the attachment section 33 preferably has an external thread, which is not shown in the attached illustrations for purely graphic reasons.

The carrier section 31 is limited in the proximal direction by a first stop 32. The first stop 32 is formed by a step resulting from different outer diameters of individual sections of the base carrier 30. Distally adjoining the carrier section 33 is a base section 36 which is cylindrical in shape but has a larger cross-sectional diameter than the carrier section 31. The stop 32 is formed by an annular surface which longitudinal-axially limits the base section 36 and is oriented substantially perpendicular to the longitudinal axis of the base carrier 30.

In the proximal direction, the base section 36 merges into a holding section 37. The holding section 37 has a substantially frustoconical outer contour, so that the holding section 37 forms a transition between the base section 36 and a clamping section 38. The clamping section 38 has an outer diameter that is larger than the outer diameter of the base section 36. Several openings are arranged in the holding section 37, which are preferably formed as blind holes aligned radially with respect to the longitudinal axis of the base carrier 30. The openings in the holding section 37 serve to receive deflection pins, which serve as deflection points for filaments 11. In this way, loops 12 can be formed on the stent to be produced, as will be explained in more detail later.

The clamping section 38, which adjoins the holding section 37, forms the interface to a braiding machine. By means of the clamping section, the braiding mandrel comprising the base carrier 30 and multiple braiding sleeves 21, 22, 23, can be clamped into a braiding machine. Thereby, the clamping section 38 is configured such that a rotationally fixed connection to the braiding machine is established when the base carrier 30 is clamped. In this way, the base carrier 30 can be rotated on the braiding machine to accomplish braiding of the stent 10.

As can also be seen in FIG. 2, the first braiding sleeve 21 is adapted to provide a substantially flush or jump-free transition between the base section 36 of the base support 30 and the outer contour of the second braiding sleeve 22. To braid the stent 10, a plurality of filaments 11 are braided over the second braiding sleeve 22, the first braiding sleeve 21 and the base section 36 up to the holding section 37. In the holding section 37, preferably a plurality of deflection pins are arranged in the respective openings. The filaments 11 are placed around the deflection pins, thereby reversing the braiding direction. The filaments 11 are then braided in the opposite direction over the base section 36, the first braiding sleeve 21 up to over the second braiding sleeve 22. In this way, a stent with three different segments is created.

In particular, the stent 10 produced by means of the braiding mandrel according to FIG. 2 can be used to treat the blood vessel according to FIG. 1. The section of the stent 10 braided over the base section 36 takes into account the parameters L53 and D53 and is suitable for insertion into the distal segment 53 of the blood vessel 50. The portion of the stent 10 braided over the first braiding sleeve 21 preferably bridges the aneurysm 54 in the middle segment 52 of the blood vessel 50. The portion of the stent 10 that has been braided over the second braiding sleeve 22 is dimensioned to take into account the parameters L51 and D51 and, in this respect, is well-fitted into the proximal segment 51 of the blood vessel 50.

FIG. 3 shows another embodiment example for a braiding mandrel formed from a base carrier and multiple braiding sleeves 21, 22, 23 of a set 20. The embodiment example according to FIG. 3 differs from the embodiment example according to FIG. 2 in that, in the embodiment example according to FIG. 3, a braiding mandrel 40 is provided which is suitable and intended for forming a stent 10 having a total of five different sections. Furthermore, a threaded nut 35 is shown in FIG. 3, which forms a second stop 34, whereby such a threaded nut 35 is preferably also provided in the embodiment example according to FIG. 2, but is not shown for drawing reasons.

The base support 30 according to FIG. 3 is of identical design to the base support 30 according to FIG. 2. It has a clamping section 38, a subsequent holding section 37 with blind holes for receiving deflection pins, an adjoining base section 36 and a carrier section 31, which merges into an attachment section 33. A first stop 32 is formed between the carrier section 31 and the base section 36.

The set 20 includes multiple braiding sleeves 21, 22, 23, wherein three braiding sleeves 21, 22, 23 have been selected to be combined with the base carrier 30 to form a braiding mandrel 30. In this regard, a first braiding sleeve 21 has an outer contour comprising a frustoconical section facing the first stop 32 and a cylindrical section adjoining the frusto-conical section. The frustoconical section forms a jump-free transition from the base section 36 to the cylindrical section of the first braiding sleeve 21.

The second braiding sleeve 22 has a similar outer contour, but the cross-sectional diameter is increased. As a result, the frustoconical section of the second braiding sleeve forms a jump-free transition from the cylindrical section of the first braiding sleeve 21 to the cylindrical section of the second braiding sleeve 22. Adjacent to the second braiding sleeve 22 is a third braiding sleeve 23, which comprises an overall cylindrical outer contour. While the first braiding sleeve 21 and the second braiding sleeve 22 have substantially equal lengths, however, the third braiding sleeve 23 comprises a length corresponding to a multiple of the length of the first braiding sleeve 21 and the second braiding sleeve 22, respectively.

The third braiding sleeve 23 is followed by the threaded nut 35, which forms the second stop 34 of the carrier section 31. The threaded nut 35 can be screwed on via an external thread of the attachment section 33, so that the three braiding sleeves 21, 22, 23 are clamped longitudinally between the first stop 32 and the threaded nut 35.

Figure 4:
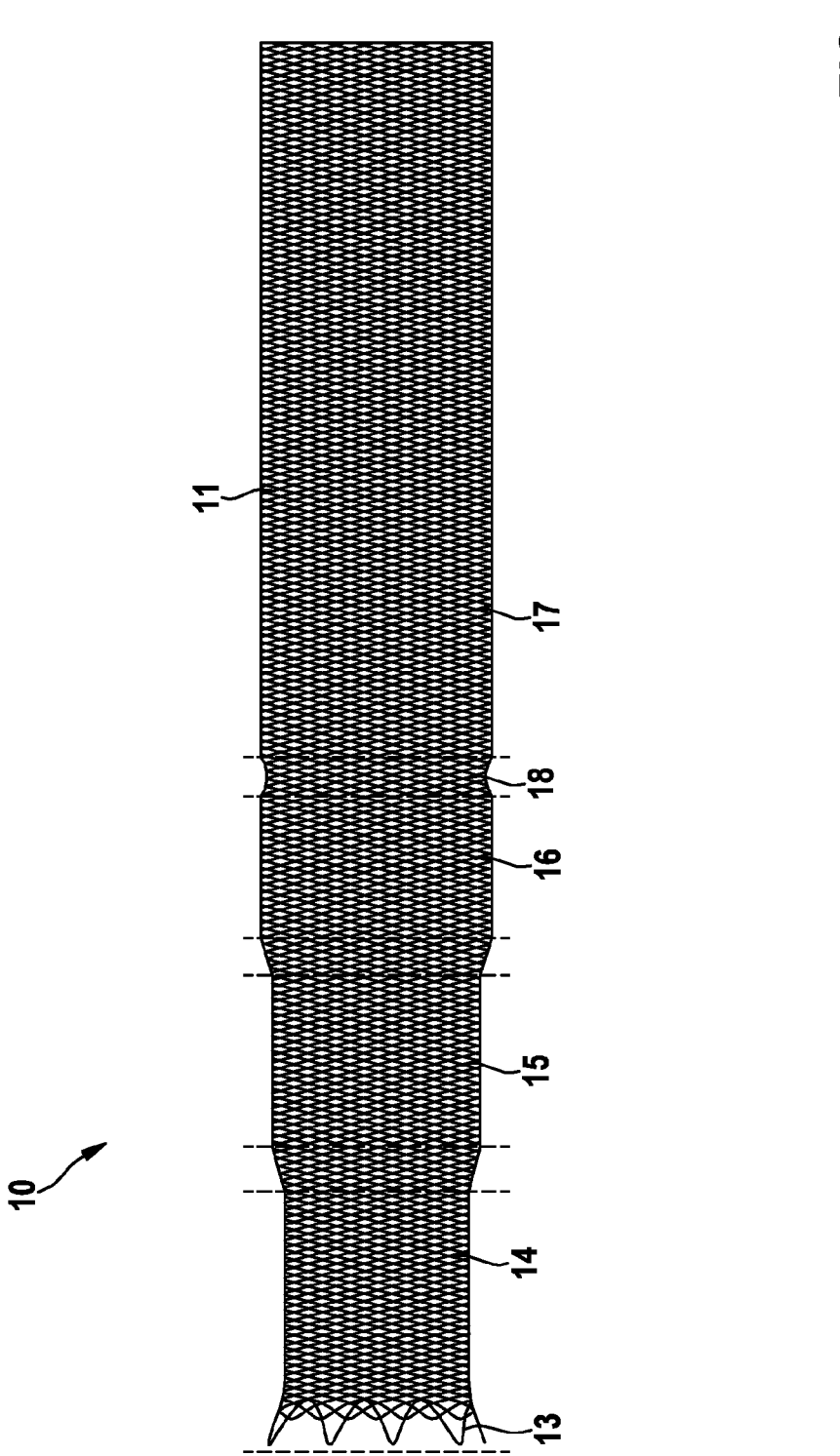
FIG. 4: a side view of a stent produced with the system according to the invention as shown in FIG. 3.

FIG. 4 shows a stent 10 formed from filaments 11. The filaments 11 may be made of metal or a polymer or a combination of a metal and a polymer. When a polymer is involved in the filament 11, it may preferably be bioresorb-able.

The stent 10 shown in FIG. 4 was produced on the braiding mandrel 40 shown in FIG. 3. Consequently, the stent 10 comprises five different sections 13, 14, 15, 16, 17, which differ in their cross-sectional diameters.

Thus, the stent 10 includes a first section 13 braided over the holding section 37 of the braiding mandrel. The first section 13 includes loops 12 formed by deflecting the individual filaments 11 over the deflection pins in the holding section 37. As can be seen particularly well in the detailed view shown in FIG. 5, the stent 10 in the first section 13 comprises a contour in which the loops 12 flare radially outward. Such a longitudinal end of a stent 10, in which the filaments 11 flare outwardly in a frustoconical shape, is also referred to as flaring.

Adjacent to the first section 13 is a second section 14 braided over the base section 36 of the base carrier 30. The second section 14 has a substantially cylindrical outer contour.

The third section 15 has been formed on the first braid sleeve 21. In this respect, the third section 15 comprises a transition section forming a substantially frustoconical sub-section. This is followed by a cylindrical shaped subsection. The transition section forms a jump-free transition between the cylindrical-shaped second section 14 and the cylindrical-shaped subsection of the third section 15. The cylindrical-shaped subsection of the third section 15 has a larger cross-sectional diameter than the second section 14.

A fourth section 16 of the stent 10 adjoins the third section 15. The fourth section 16 also comprises a transition section formed as a subsection having a frustoconical outer contour. Adjacent to the frustoconical subsection is a cylindrical subsection. The cylindrical subsection of the section 16 comprises a cross-sectional diameter larger than the cross-sectional diameter of the cylindrical subsection of the third section 15. The frustoconical subsection of the fourth section 16 forms a jump-free transition from the cylindrical subsection of the third section 15 to the cylindrical subsection of the fourth section 16.

The fourth section 16 is followed by a fifth section 17. The fifth section 17 is substantially longer than the previous sections 13, 14, 15, 16. The fifth section 17 was formed by braiding the filaments 11 over the third braiding sleeve 23 as shown in FIG. 3. In this respect, the fifth section 17 has a cross-sectional diameter substantially equal to the cross-sectional diameter of the cylindrical subsection of the fourth section 16.

In FIG. 4, it can also be seen that the fifth section 17 comprises an intermediate section 18. However, the inter-mediate section 18 is not defined by the outer contour of the braided mandrel 40 used to form the stent 10. Rather, the stent 10 has a different porosity in the intermediate section 18 than in the other sections 13, 14, 15, 16. This change in porosity is achieved by varying the braiding angle during the braiding of the filaments 11 over the braiding mandrel 40. Thus, a different braiding angle has been set in the inter-mediate section 18 than in the other sections 13, 14, 15, 16, 17.

Figure 6:
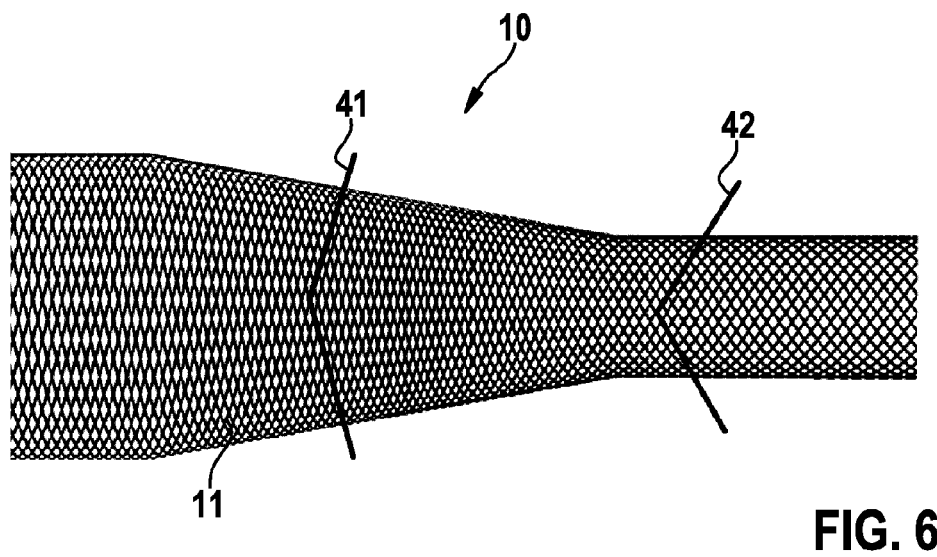
FIG. 6: a side view of a stent produced with the system according to the invention, according to another preferred embodiment.

The change in the braiding angle can be seen more clearly than in FIG. 4 in the embodiment example shown in FIG. 6. Therein, a first braiding angle 41 and a second braiding angle 42 are shown. In that the first braiding angle 41 is larger than the second braiding angle 42, a uniform porosity is set over the entire stent 10, although the cross-sectional diameter of the stent 10 obviously changes.

Figure 5:
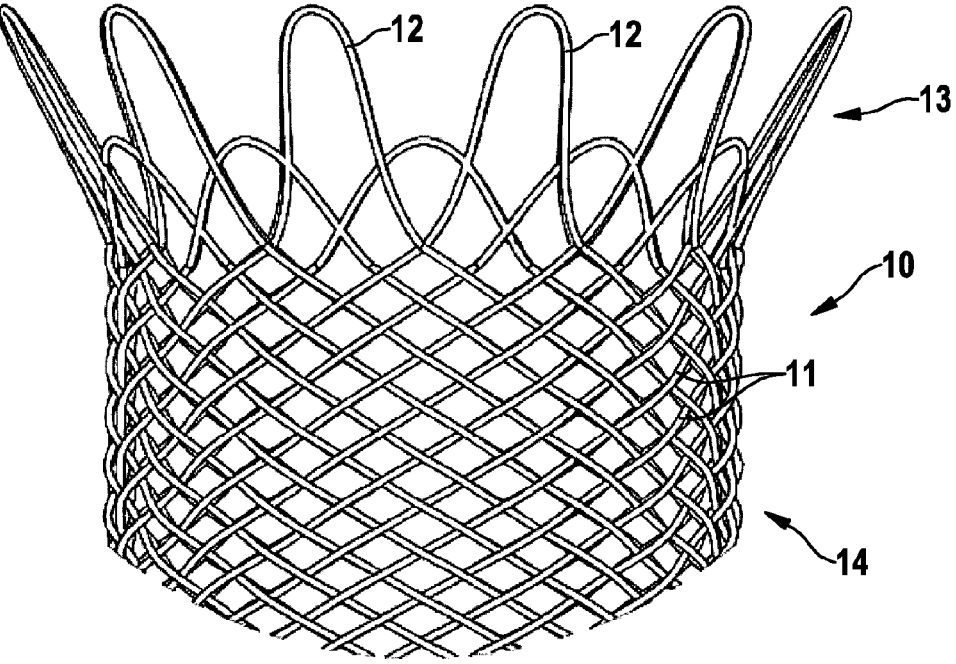
FIG. 5: a detailed view of a longitudinal end of the stent according to FIG. 4.

FIG. 5 shows in detail a longitudinal end of the stent 10 according to FIG. 4, in particular the first section 13 and a part of the second section 14 of the stent 10. With regard to the first section 13, it can be seen that it is characterized by loops 12, wherein the loops 12 have different lengths. Specifically, every second loop 12 is formed as a long loop. A short loop 12 is located between two long loops 12. The different lengths of the loops 12 can be produced by arranging the blind holes in the holding section 37 of the base carrier 30 offset from each other. This can also be seen in FIGS. 2 and 3.

Preferably, it is provided that the length ratio between the long loops 12 to the short loops 12 is between 1 and 8, preferably the length ratio can be between 3 and 4, ideally 3.6.

The filaments 11 of the stent 10 preferably comprise a superelastic material, in particular a nickel-titanium alloy. The cross-sectional diameter of the filaments 11 may be between 0.02 mm and 0.08 mm. Preferably, the cross-sectional diameter of the filaments 11 is between 0.03 mm and 0.05 mm.

In order to form a mesh as tight as possible for the stent 10, it is preferred that the number of filament crossings that show on a circumferential line of the stent 10 is between 16 and 96, in particular between 24 and 32.

For good radiopacity of the produced stent 10, it is preferred if at least some of the filaments 11 are formed as DFT wires. In particular, between 50% and 100% of the filaments 11 of the stent 10 can be formed as DFT wires. Particularly preferred is an embodiment in which all filaments 11 are formed as DFT wires. Furthermore, it is preferred if the cross-sectional area of the radiopaque material in the DFT wire is between 20% and 40% of the total cross-sectional area. In particular, the cross-sectional area of the X-ray visible core material relative to the total cross-sectional area of the wire 11 may be 30%.

The preferably formed flaring at a longitudinal end of the stent 10, i.e. the radial widening of the loops 12, is preferably performed at an angle relative to the longitudinal axis of the stent 10 of 10° to 40°, in particular 20° to 35°, preferably 30°.

The braiding angle at which the filaments 11 are braided over the braiding mandrel 40 is preferably at least 45°, more preferably between 60° and 80°, more preferably between 70° and 75°. When the braiding angle is varied over the length of the stent 10 to ensure constant porosity over all sections 13, 14, 15, 16, 17, it is preferably provided that the stent is braided at a constant pull-off speed. In particular, the braiding angle can be varied at the transition from the second section 14 to the first section 13, i.e. at the transition into a loop 12, the braiding angle at this point preferably also being at least 45°, in particular between 50° and 75°, in particular between 60° and 70°.

The largest outer diameter of the braiding mandrel, in particular of the braiding sleeves 21, 22, 23 of the set 20 is preferably between 1.5 mm and 10 mm, in particular between 2.5 mm and 8 mm. Thus, stents 10 with a corresponding inner diameter can be formed. Stents with such maximum outer dimensions are particularly suitable for the treatment of blood vessels in the cerebral area.

To ensure a good radial force, in particular also at the longitudinal end of the stent 10, it is preferred if the inner radii of the loops 12 at the longitudinal end of the stent are 0.15 mm and 0.5 mm, in particular between 0.2 mm and 0.3 mm.

LIST OF REFERENCE NUMERALS

10 stent
11 filament
12 loop
13 first section
14 second section
15 third section
16 fourth section

17 fifth section
18 intermediate section
20 set
21 first braiding sleeve
22 second braiding sleeve
23 third braiding sleeve
24 through opening
30 base carrier
31 carrier section
32 first stop
33 attachment section
34 second stop
35 threaded nut
36 base section
37 holding section
38 clamping section
40 braiding mandrel
41 first braiding angle
42 second braiding angle
50 blood vessel
51 proximal segment
52 middle segment
53 distal segment
L51 length of the proximal segment
L52 length of the middle segment
L53 length of the distal segment
D51 diameter of the proximal segment
D53 diameter of the distal segment

The invention claimed is:

1. A system configured to braid a patient-specific adapted stent, the system comprising:
   at least one set with multiple braiding sleeves and a base carrier configured to receive at least two braiding sleeves of the at least one set, wherein each braiding sleeve has an inner contour adapted to an outer contour of the base carrier, so that the multiple braiding sleeves are adapted to be arranged in any order on the base carrier to form a braiding mandrel, and wherein the at least two braiding sleeves of the at least one set have different outer contours from each another.

2. The system according to claim 1, wherein the at least two braiding sleeves of the at least one set have different lengths from each other.

3. The system according to claim 1, wherein the base carrier has at least one cylindrical carrier section and each braiding sleeve has a through opening so that the multiple braiding sleeves are adapted to be slid onto the carrier section with a loose fit.

4. The system according to claim 3, wherein the base carrier has, at a first longitudinal end of the carrier section, a first stop for the multiple braiding sleeves and, at a second longitudinal end of the carrier section, an attachment section configured to receive a removable second stop.

5. The system according to claim 4, wherein a distance between the first stop and the removable second stop is variable such that the multiple braiding sleeves slid onto the carrier section are adapted to be fixed longitudinal-axially between the first stop and the removable second stop.

6. The system according to claim 4, wherein the attachment section has an external thread and the second stop is formed by a threaded nut.

7. A method for braiding a patient-specific adapted stent, the method comprising:
   selecting braiding sleeves from a set, wherein at least two braiding sleeves of the set have different outer contours from each other;

arranging the braiding sleeves on a base carrier to form a braiding mandrel, wherein the braiding sleeves directly abut each other; and braiding the stent from one or more filaments on the braiding mandrel.

8. The method according to claim 7, wherein selecting braiding sleeves comprises:

detecting an inner contour of a blood vessel to be treated with the stent; and targeting selection of the braiding sleeves which in combination form an outer contour adapted to the inner contour of the blood vessel.

9. The method according to claim 7, wherein selecting braiding sleeves comprises selecting the at least two braiding sleeves.

10. The method according to claim 7, wherein braiding the stent comprises varying a braiding angle to establish a uniform porosity over an entire length of the stent.

11. The method according to claim 7, wherein braiding the stent comprises reversing a braiding direction of the filaments to form loops at a longitudinal end of the stent.

12. The method according to claim 7, wherein the stent is braided from the filaments comprising a radiopaque core material and a sheath material of a shape memory alloy.

13. The method according to claim 7, wherein the at least two braiding sleeves of the set have different lengths from each other.

14. The method according to claim 7, wherein at least one braiding sleeve of the set has an outer contour or length produced on a basis of image data of a blood vessel of an individual patient.

15. The method according to claim 7, wherein the base carrier has at least one cylindrical carrier section and each braiding sleeve has a through opening so that the braiding sleeves are adapted to be slid onto the carrier section with a loose fit.

16. A system configured to braid a patient-specific adapted stent, the system comprising:

at least one set with multiple braiding sleeves and a base carrier configured to receive at least two braiding sleeves of the at least one set, wherein each braiding sleeve has an inner contour adapted to an outer contour of the base carrier, so that the multiple braiding sleeves are adapted to be arranged in any order on the base carrier to form a braiding mandrel, wherein the at least two braiding sleeves of the at least one set have different outer contours from each another, and wherein the base carrier has at least one cylindrical carrier section and each braiding sleeve has a through opening so that the multiple braiding sleeves are adapted to be slid onto the carrier section with a loose fit.

17. The system according to claim 16, wherein the base carrier has, at a first longitudinal end of the carrier section, a first stop for the multiple braiding sleeves and, at a second longitudinal end of the carrier section, an attachment section configured to receive a removable second stop.

18. The system according to claim 17, wherein a distance between the first stop and the removable second stop is variable such that the multiple braiding sleeves slid onto the carrier section are adapted to be fixed longitudinal-axially between the first stop and the removable second stop.

19. The system according to claim 17, wherein the attachment section has an external thread and the removable second stop is formed by a threaded nut.

* * * * *